(12) United States Patent
Ochiai et al.

(10) Patent No.: US 11,327,047 B2
(45) Date of Patent: May 10, 2022

(54) GAS ANALYSIS APPARATUS AND GAS ANALYSIS METHOD

(71) Applicant: HORIBA, LTD., Kyoto (JP)

(72) Inventors: Ryota Ochiai, Kyoto (JP); Tomoshi Yoshimura, Kyoto (JP); Ma Camille Corrales Lacdan, Kyoto (JP)

(73) Assignee: HORIBA, LTD., Kyoto (JP)

( * ) Notice: Subject to any disclaimer, the term of this patent is extended or adjusted under 35 U.S.C. 154(b) by 495 days.

(21) Appl. No.: 16/536,707

(22) Filed: Aug. 9, 2019

(65) Prior Publication Data
US 2020/0057024 A1    Feb. 20, 2020

(30) Foreign Application Priority Data

Aug. 17, 2018  (JP) .............................. JP2018-153721

(51) Int. Cl.
  *G01N 27/62*  (2021.01)
  *G01N 27/626*  (2021.01)
  *G01N 1/40*  (2006.01)

(52) U.S. Cl.
  CPC .......... *G01N 27/626* (2013.01); *G01N 1/4044* (2013.01)

(58) Field of Classification Search
  CPC ........... G01N 33/0006; G01N 33/0011; G01N 33/0013; G01N 33/0014; G01N 33/0016; G01N 33/0018; G01N 33/0024; G01N 33/0047; G01N 33/225; G01N 1/22; G01N 1/2252; G01N 1/4044; G01N 30/68;
  (Continued)

(56) References Cited

U.S. PATENT DOCUMENTS

2017/0106328 A1* 4/2017 Montgomery ..... B01D 53/0446
2017/0292423 A1* 10/2017 Yoshida ................ F01N 3/0871
(Continued)

FOREIGN PATENT DOCUMENTS

EP       3553491 A1   10/2019
JP    2002-350304 A   12/2002
(Continued)

OTHER PUBLICATIONS

EESR dated Feb. 17, 2020 issued for European Patent Application No. 19190841.7, 8 pgs.

*Primary Examiner* — Thang X Le
(74) *Attorney, Agent, or Firm* — Brooks Kushman P.C.

(57) ABSTRACT

The present invention includes a first flow path through which a sample gas flows, a first analyzer that is provided in the first flow path to measure total hydrocarbon concentration in the sample gas, a second flow path through which the sample gas flows, a non-methane non-ethane cutter that is provided in the second flow path to remove the hydrocarbon components other than the methane and the ethane in the sample gas, a second analyzer that is provided downstream of the non-methane non-ethane cutter in the second flow path to measure the total methane ethane concentration of the methane and the ethane in the sample gas, and a calculation part that calculates the concentration of the hydrocarbon components other than the methane and the ethane in the sample gas with use of the total hydrocarbon concentration by the first analyzer and the total methane ethane concentration by the second analyzer.

17 Claims, 5 Drawing Sheets

(58) Field of Classification Search
CPC ...... G01N 30/84; G01N 30/88; G01N 27/626; G01N 2030/8405; G01N 2030/8854
See application file for complete search history.

(56) References Cited

U.S. PATENT DOCUMENTS

| | | |
|---|---|---|
| 2018/0095063 A1 | 4/2018 | Staller et al. |
| 2018/0163666 A1* | 6/2018 | Mohara .............. G01N 33/0016 |
| 2019/0391045 A1* | 12/2019 | Yoshimura .......... G01M 15/102 |

FOREIGN PATENT DOCUMENTS

| | | |
|---|---|---|
| WO | 03-001196 A1 | 1/2003 |
| WO | 2018105169 A1 | 6/2018 |

* cited by examiner

GAS ANALYSIS APPARATUS AND GAS ANALYSIS METHOD

CROSS-REFERENCE TO RELATED APPLICATION

This application claims priority to Japanese Application No. 2018-153721, filed Aug. 17, 2018, the disclosure of which is incorporated in its entirety by reference herein.

TECHNICAL FIELD

The present invention relates to a gas analysis apparatus and a gas analysis method.

BACKGROUND ART

In the past, there has been considered a gas analysis apparatus that obtains the concentration of non-methane hydrocarbons (NMHC) defined as total hydrocarbons (THC) contained in exhaust gas without methane ($CH_4$).

This gas analysis apparatus is configured with use of detectors using a hydrogen flame ionization method (flame ionization detectors (FID)), and allows one detector to measure THC concentration in the exhaust gas, as well as allows the other detector to measure $CH_4$ concentration contained in the exhaust gas passing through a non-methane cutter (NMC) for removing hydrocarbon components other than the methane in the exhaust gas. Then, the gas analysis apparatus calculates the concentration of the hydrocarbon components other than the methane (NMHC) from the difference between the concentrations obtained by the detectors.

The role of the NMC is to oxidize and remove the hydrocarbon components other than the methane using a catalytic effect, and the performance thereof is evaluated on the basis of a ratio at which the NMC allows the methane to penetrate therethrough and a ratio at which the NMC allows ethane to penetrate therethrough, which is the second hardest to oxidize. The former is referred to as methane penetration efficiency, and it is considered that the higher the efficiency, the higher the performance, whereas the latter is referred to as ethane penetration efficiency, and it is considered that the lower the efficiency, the higher the performance. A methane penetration efficiency of 85% or more and an ethane penetration efficiency of 2% or less are required.

CITATION LIST

Patent Literatures

Patent Literature 1: Japanese Unexamined Patent Application Publication No. 2002-350304

SUMMARY OF INVENTION

Technical Problem

Meanwhile, in recent years, with increasing natural gas recoverable amount, the natural gas vehicle market has been expanding. For this reason, a demand to measure natural gas vehicles has also been increasing. The components of natural gas are mainly methane and ethane, and large amounts of these components are also contained in exhaust gas of natural gas vehicles. However, the contribution of methane and ethane to atmospheric pollution such as photochemical smog is low, and it has been required to exclude them from regulation targets and measure the concentration of hydrocarbons other than methane and ethane (non-methane non-ethane hydrocarbons (NMNEHC)). In addition, as a method for measuring the concentration of NMNEHC, the use of GC-FID is considered.

However, when measuring the concentration of NMNEHC using GC-FID, it is necessary to flow sample gas through a column filled with a filler and separate respective components on the basis of differences in transit time. However, continuous measurement cannot be performed because of batch measurement.

Therefore, the present invention has been made in order to solve the above-described problem, and a main object thereof is to make it possible to continuously measure the concentration of hydrocarbon components other than methane and ethane (NMNEHC) in sample gas.

Solution to Problem

That is, the gas analysis apparatus according to the present invention includes: a first flow path through which sample gas flows; a first analyzer that is provided in the first flow path to measure total hydrocarbon concentration in the sample gas; a second flow path through which the sample gas flows; a non-methane non-ethane cutter that is provided in the second flow path to remove hydrocarbon components other than methane and ethane in the sample gas; a second analyzer that is provided downstream of the non-methane non-ethane cutter in the second flow path to measure the total methane ethane concentration of the methane and the ethane in the sample gas; and a calculation part that calculates the concentration of the hydrocarbon components other than the methane and the ethane in the sample gas with use of the total hydrocarbon concentration by the first analyzer and the total methane ethane concentration by the second analyzer.

In such a configuration, since the total methane ethane concentration of the methane and the ethane in the sample gas can be continuously measured by the second analyzer with use of the non-methane non-ethane cutter that removes the hydrocarbon components other than the methane and the ethane, the concentration of the hydrocarbon components other than the methane and the ethane in the sample gas can be calculated in combination with the THC concentration continuously measured by the first analyzer. As a result, the concentration of the hydrocarbon components other than the methane and the ethane (NMNEHC) in the sample gas can be continuously measured.

Specifically, it is considered that the calculation part calculates the concentration of the hydrocarbon components other than the methane and the ethane in the sample gas with use of the total hydrocarbon concentration by the first analyzer, the total methane ethane concentration by the second analyzer, and specific organic matter penetrability that is a ratio at which specific organic matter having a carbon number of 3 or more passes through the non-methane non-ethane cutter.

In detail, it is considered that the calculation part calculates the concentration of the hydrocarbon components other than the methane and the ethane in the sample gas in accordance with an expression below.

[Expression 1]

$$x_{NMNEHC} = \frac{x_{THC[THC-FID]} - x_{THC[NMNEC-FID]}}{1 - PF_{C_3H_8[NMNEC-FID]}} \quad (1)$$

$x_{NMNEHC}$: the concentration of the hydrocarbon components other than the methane and the ethane in the sample gas $x_{THC[THC-FID]}$: the total hydrocarbon concentration by the first analyzer $x_{THC[NMNEC-FID]}$: the total methane ethane concentration by the second analyzer, $PF_{C3H8[NMNEC-FID]}$: the specific organic matter penetrability that is a ratio at which the specific organic matter having a carbon number of 3 or more (in this case, propane) passes through the non-methane non-ethane cutter The above expression is based on the assumption that the second analyzer is calibrated with ethane used and passed through the non-methane non-ethane cutter.

It is desirable that the gas analysis apparatus of the present invention further includes: a third flow path through which the sample gas flows; a non-methane cutter that is provided in the third flow path to remove hydrocarbon components other than the methane in the sample gas; and a third analyzer that is provided downstream of the non-methane cutter in the third flow path to measure methane concentration in the sample gas.

In this configuration, it is desirable that the calculation part calculates the concentration of the hydrocarbon components other than the methane (NMHC) in the sample gas with use of the total hydrocarbon concentration by the first analyzer and the methane concentration by the third analyzer.

Also, it is desirable that the calculation part calculates ethane concentration in the sample gas with use of the total methane ethane concentration by the second analyzer and the methane concentration by the third analyzer.

In order for the non-methane non-ethane cutter to efficiently remove the hydrocarbon components other than the methane and the ethane and to allow the methane and the ethane to selectively pass therethrough, it is desirable that the second flow path is provided with a heating part that increases the temperature of the non-methane non-ethane cutter to 200 to 250° C.

In order for the non-methane cutter to efficiently remove the hydrocarbon components other than the methane and to allow the methane to selectively pass therethrough, it is desirable that the third flow path is provided with a heating part that increases the temperature of the non-methane cutter to 300° C. or more.

Providing the non-methane non-ethane cutter in the second flow path differentiates response timing between the first analyzer and the second analyzer, thus making it difficult to accurately analyze the concentration of the hydrocarbon components other than the methane and the ethane in the sample gas.

In order to preferably solve this problem, it is desirable that the gas analysis apparatus of the present invention further includes: a first flow rate regulating mechanism provided in the first flow path; and a second flow rate regulating mechanism provided in the second flow path, and the first flow rate regulating mechanism and the second flow rate regulating mechanism match the response timing between the first analyzer and the second analyzer.

Similarly, providing the non-methane cutter in the third flow path differentiates response timing among the first analyzer, the second analyzer, and the third analyzer, thus making it difficult to accurately analyze the concentration of each component.

It is desirable that the gas analysis apparatus of the present invention further includes a third flow rate regulating mechanism provided in the third flow path, and the first flow rate regulating mechanism, the second flow rate regulating mechanism, and the third flow rate regulating mechanism match the response timing among the first analyzer, the second analyzer, and the third analyzer.

Also, the gas analysis apparatus according to the present invention includes: a flow path through which sample gas flows; a hydrocarbon selective catalyst that is provided in the flow path to remove a predetermined hydrocarbon component in the sample gas; an analyzer that is provided downstream of the hydrocarbon selective catalyst in the flow path to measure the concentration of hydrocarbon components in the sample gas; and a temperature switching mechanism that switches the temperature of the hydrocarbon selective catalyst. In addition, the temperature switching mechanism heats the hydrocarbon selective catalyst to 200 to 250° C. to make the hydrocarbon selective catalyst serve as a non-methane non-ethane cutter that removes hydrocarbon components other than methane and ethane in the sample gas, and heats the hydrocarbon selective catalyst to 300° C. or more to make the hydrocarbon selective catalyst serve as a non-methane cutter that removes hydrocarbon components other than the methane in the sample gas.

This gas analysis apparatus is capable of measuring not only the concentration of the hydrocarbon components other than the methane and the ethane (NMNEHC) in the sample gas but the concentration of the hydrocarbon components other than the methane (NMHC) in the sample gas. Also, the non-methane non-ethane cutter and the non-methane cutter can be configured using the hydrocarbon selective catalyst in common, and a flow path configuration can be simplified.

Further, the gas analysis method according to the present invention is one: providing a first analyzer, which measures total hydrocarbon concentration in sample gas, in a first flow path through which the sample gas flows; providing a non-methane non-ethane cutter, which removes hydrocarbon components other than methane and ethane in the sample gas, in a second flow path through which the sample gas flows: providing a second analyzer, which measures the total methane ethane concentration of the methane and the ethane in the sample gas, downstream of the non-methane non-ethane cutter in the second flow path; and calculating the concentration of the hydrocarbon components other than the methane and the ethane in the sample gas with use of the total hydrocarbon concentration by the first analyzer and the total methane ethane concentration by the second analyzer.

Still further, a gas analysis apparatus calibration method according to the present invention is a calibration method for a gas analysis apparatus including: a first flow path through which sample gas flows; a first analyzer that is provided in the first flow path to measure total hydrocarbon concentration in the sample gas; a second flow path through which the sample gas flows; a non-methane non-ethane cutter that is provided in the second flow path to remove hydrocarbon components other than methane and ethane in the sample gas; a second analyzer that is provided downstream of the non-methane non-ethane cutter in the second flow path to measure the total methane ethane concentration of the methane and the ethane in the sample gas; and a calculation part that calculates the concentration of the hydrocarbon components other than the methane and the ethane in the sample gas with use of the total hydrocarbon concentration by the first analyzer and the total methane ethane concentration by the second analyzer. In addition, the gas analysis apparatus calibration method calibrates the second analyzer with ethane used and passed through the non-methane non-ethane cutter. Also, it is desirable that the first analyzer is calibrated with use of propane.

Yet further, the gas analysis method according to the present invention is one using a gas analysis apparatus including: a first flow path through which sample gas flows; a first analyzer that is provided in the first flow path to measure total hydrocarbon concentration in the sample gas; a second flow path through which the sample gas flows; a non-methane non-ethane cutter that is provided in the second flow path to remove hydrocarbon components other than methane and ethane in the sample gas; and a second analyzer that is provided downstream of the non-methane non-ethane cutter in the second flow path to measure the total methane ethane concentration of the methane and the ethane in the sample gas. In addition, the gas analysis method uses Expression (A) below in the case where the first analyzer is calibrated with use of propane:

$$x_{THC[THC\text{-}FID]} = x_{CH4} \times RF_{CH4[THC\text{-}FID]} + x_{C2H6} \times RF_{C2H6[THC\text{-}FID]} + x_{NMNEHC} \quad \text{Expression (A):}$$

$x_{THC[THC\text{-}FID]}$: the total hydrocarbon concentration by the first analyzer $x_{CH4}$: methane concentration in the sample gas $RF_{CH4[THC\text{-}FID]}$: a methane response factor in the first analyzer $x_{C2H6}$: ethane concentration in the sample gas $RF_{C2H6[THC\text{-}FID]}$: an ethane response factor in the first analyzer $x_{NMNEHC}$: the concentration of the hydrocarbon components other than the methane and the ethane in the sample gas, and Expression (B) below in the case where the second analyzer is calibrated with ethane used and passed through the non-methane non-ethane cutter:

$$x_{THC[NMNEC\text{-}FID]} = x_{CH4} \times RF_{CH4[NMNEC\text{-}FID]} \times PF_{CH4[NMNEC\text{-}FID]} + x_{C2H6} + x_{NMNEHC} \times RF_{C3H8[NMNEC\text{-}FID]} \times PF_{C3H8[NMNEC\text{-}FID]} \quad \text{Expression (B):}$$

$x_{THC[NMNEC\text{-}FID]}$: the total methane ethane concentration by the second analyzer $RF_{CH4[NMNEC\text{-}FID]}$: a methane response factor in the second analyzer $PF_{CH4[NMNEC\text{-}FID]}$: methane penetrability in the second analyzer $RF_{C3H8[NMNEC\text{-}FID]}$: a propane response factor in the second analyzer $PF_{C3H8[NMNEC\text{-}FID]}$: propane penetrability in the second analyzer to derive Expression (1) below:

[Expression 2]

$$x_{NMNEHC} = \frac{x_{THC[THC-FID]} - x_{THC[NMNEC-FID]}}{1 - PF_{C_3H_8[NMNEC-FID]}} \quad (1)$$

$x_{NMNEHC}$: the concentration of the hydrocarbon components other than the methane and the ethane in the sample gas $x_{THC[THC\text{-}FID]}$: the total hydrocarbon concentration by the first analyzer $x_{THC[NMNEC\text{-}FID]}$: the total methane ethane concentration by the second analyzer $PF_{C3H3[NMNEC\text{-}FID]}$: specific organic matter penetrability that is a ratio at which specific organic matter having a carbon number of 3 or more (in this case, propane $C_3H_8$) passes through the non-methane non-ethane cutter, and calculates the concentration of the hydrocarbon components other than the methane and the ethane in the sample gas with use of Expression (1) above.

Also, it is desirable to,
in Expression (A) above, consider the ethane response factor $RF_{C2H6[THC\text{-}FID]}$ as 1.0 to derive Expression (A') below:

$$x_{THC[THC\text{-}FID]} = x_{CH4} \times RF_{CH4[THC\text{-}FID]} + x_{C2H6} + x_{NMNEHC} \quad \text{Expression (A'):}$$

in the Expression (B), consider $PF_{CH4[NMNEC\text{-}FID]}$ as 1.0, and also consider the propane response factor in the second analyzer subjected to ethane calibration as 1.0 to derive Expression (B') below:

$$x_{THC[NMNEC\text{-}FID]} = x_{CH4} \times RF_{CH4[NMNEC\text{-}FID]} + x_{C2H6} + x_{NMNEHC} \times PF_{C3H8[NMNEC\text{-}FID]} \quad \text{Expression (B'):}$$

derive Expression (C) below because when the first analyzer and the second analyzer are the same in configuration, $RF_{CH4[THC\text{-}FID]}$ and $RF_{CH4[NMNEC\text{-}FID]}$ are the same:

$$x_{THC[THC\text{-}FID]} = x_{THC[NMNEC\text{-}FID]} - x_{NMNEC} \times PF_{C3H8[NMNEC\text{-}FID]} + x_{NMNEHC} \quad \text{Expression (C):}$$

and derive Expression (1) above from Expression (C).

Advantageous Effects of Invention

According to the present invention described above, the concentration of the hydrocarbon components other than the methane and the ethane in the sample gas can be continuously measured.

DESCRIPTION OF EMBODIMENTS

In the following, a gas analysis apparatus according to one embodiment of the present invention will be described with reference to the drawings.

<Apparatus Configuration>

The gas analysis apparatus 100 of the present embodiment is one that, for example, analyzes hydrocarbons contained in exhaust gas discharged from an internal combustion engine.

Figure 1:
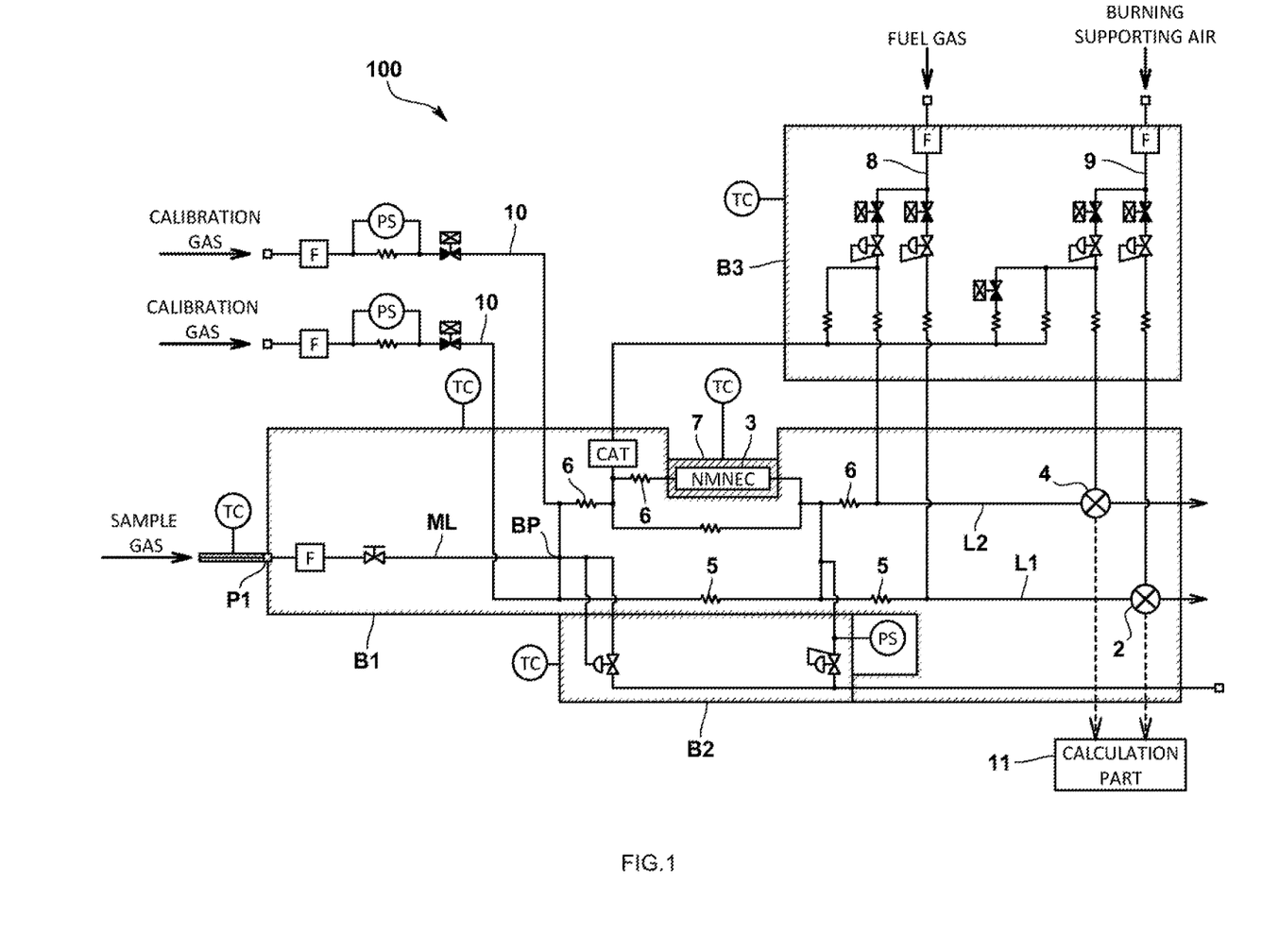
FIG. 1 is a diagram schematically illustrating the configuration of a gas analysis apparatus in the present embodiment.

Specifically, as illustrated in FIG. 1, the gas analysis apparatus 100 includes: a first flow path L1 through which exhaust gas as sample gas flows; a first analyzer 2 that is provided in the first flow path L1 to measure total hydrocarbon concentration (THC concentration) in the exhaust gas; a second flow path L2 that is provided separately from the first flow path L1 and through which the exhaust gas flows; a non-methane non-ethane cutter (NMNEC) 3 that is provided in the second flow path L2 to remove hydrocarbon components other than methane and ethane (NMNEHC) in the exhaust gas; and a second analyzer 4 that is provided downstream of the NMNEC 3 in the second flow path L2 to measure the total methane ethane concentration of the methane and the ethane in the exhaust gas.

The first flow path L1 and the second flow path L2 in the present embodiment branch from a predetermined branching point BP in a main flow path ML having an introduction port P1 through which the exhaust gas is introduced.

The first flow path L1 and the second flow path L2 are respectively provided with a first flow rate regulating mechanism 5 and a second flow rate regulating mechanism 6 so as to match response timing between the first analyzer 2 and the second analyzer 4.

The first flow rate regulating mechanism 5 is formed of, for example, a capillary provided on the upstream side of the first analyzer 2 in the first flow path L1, and the second flow rate regulating mechanism 6 is formed of, for example, a capillary provided on the upstream side of the second analyzer 4 in the second flow path L2.

Figure 2:
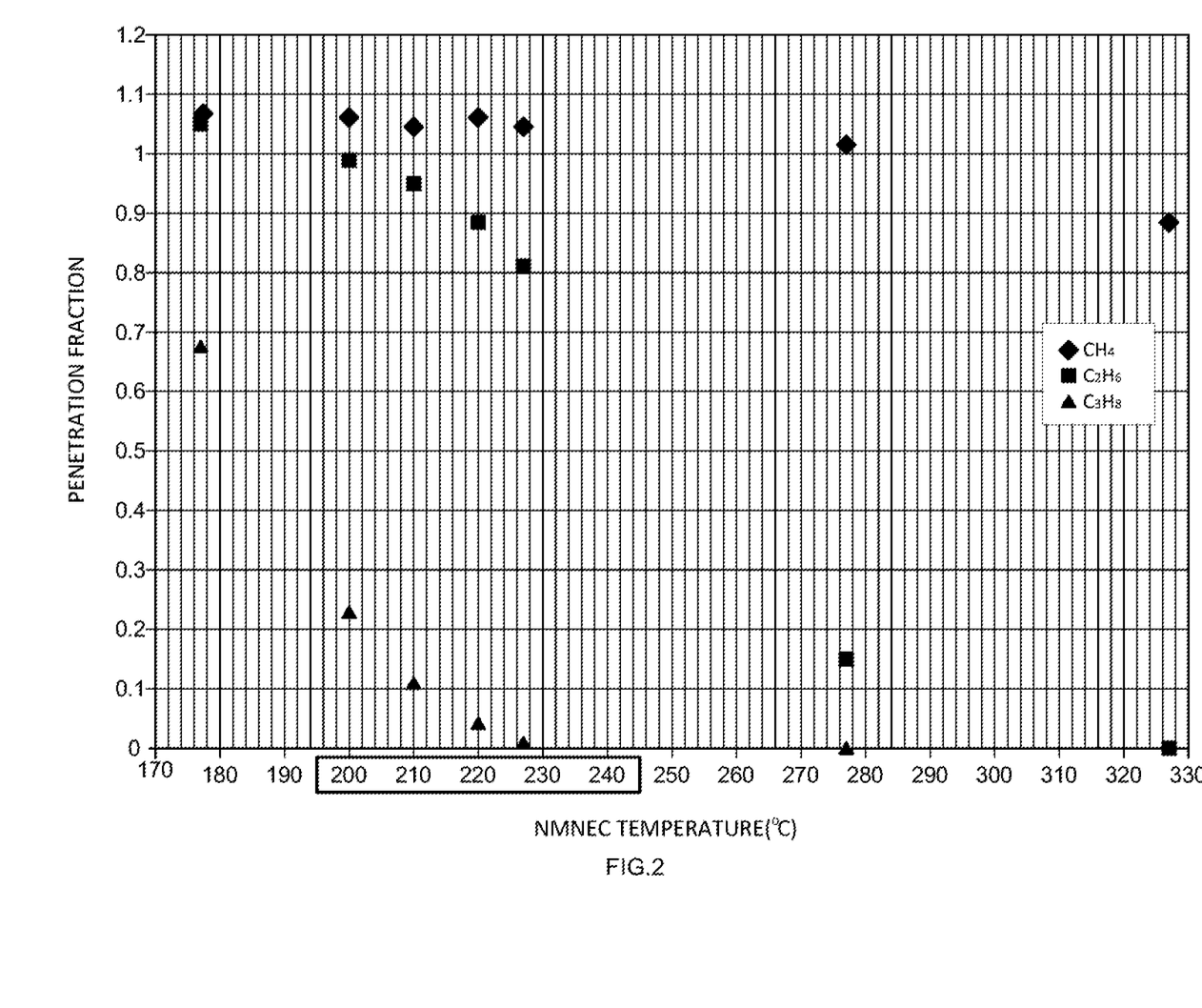
FIG. 2 is a graph illustrating the relationships between the temperature of NMNEC and the permeabilities of hydrocarbons in the same embodiment.

The NMNEC 3 provided in the second flow path L2 is an oxidation catalyst, which can use manganese dioxide or may be another metal serving as an oxidation catalyst. Also, the NMNEC 3 is heated to 200 to 250° C. Specifically, the second flow path L2 is provided with a heating part 7 for heating the NMNEC 3 to that temperature. As illustrated in FIG. 2, by heating to that temperature, the NMNEC 3 can efficiently burn and remove the hydrocarbon components other than the methane and the ethane (in FIG. 2, propane $C_3H_8$) and allow the methane and the ethane to pass therethrough efficiently (e.g., 80% or more).

Each of the first analyzer 2 and the second analyzer 4 is an FID that detects hydrocarbons in the exhaust gas by a hydrogen flame ionization (FID) method. The FID is supplied with fuel gas (e.g., $H_2$ or mixed gas of $H_2$ and He) and burning supporting air. In FIG. 1, reference sign 8 represents a fuel gas supply line for supplying the fuel gas to the first analyzer 2 and the second analyzer 4, and reference sign 9 represents a burning supporting air supply line for supplying the burning supporting air to the first analyzer 2 and the second analyzer 4. In addition, reference sign 10 represents calibration gas supply lines respectively for supplying calibration gas for calibrating the first analyzer 2 and the second analyzer 4. Further, in the gas analysis apparatus 100, the respective analyzers 2 and 4 and the respective flow paths are heated to a predetermined temperature by heating blocks B1 to B3.

Also, the gas analysis apparatus 100 includes a calculation part 11 that calculates the concentration of the NMNEHC in the exhaust gas from the respective concentrations obtained by the first analyzer 2 and the second analyzer 4.

The calculation part 11 is one that calculates the concentration of the hydrocarbon components other than the methane and the ethane in the sample gas using the total hydrocarbon concentration by the first analyzer 2 and the total methane ethane concentration by the second analyzer 4.

Specifically, the calculation part 11 calculates the NMNEHC concentration in accordance with the following expression using the THC concentration $x_{THC\text{-}[THC\text{-}FID]}$ by the first analyzer 2, the total methane ethane concentration $x_{THC[NMNEC\text{-}FID]}$ by the second analyzer 4, and specific organic matter penetrability $PF_{C_3H_8[NMNEC\text{-}FID]}$ that is a ratio at which specific organic matter having a carbon number of 3 or more (in this case, propane $C_3H_8$) passes through the NMNEC 3.

[Expression 3]

$$x_{NMNEHC} = \frac{x_{THC[THC\text{-}FID]} - x_{THC[NMNEC\text{-}FID]}}{1 - PF_{C_3H_8[NMNEC\text{-}FID]}} \quad (1)$$

The derivation of Expression (1) above will be described below.

The THC concentration $x_{THC\text{-}[THC\text{-}FID]}$ obtained by the first analyzer 2 is given by the following expression using a methane response factor $RF_{CH4\text{-}[THC\text{-}FID]}$ in the first analyzer 2, an ethane response factor $RF_{C2H6\text{-}[THC\text{-}FID]}$ in the first analyzer 2, methane concentration $x_{CH4}$ in the sample gas, ethane concentration $x_{C2H6}$ in the sample gas, and the concentration $x_{NMNEHC}$ of the hydrocarbon components other than the methane and the ethane in the sample gas.

$$x_{THC[THC\text{-}FID]} = x_{CH4} \times RF_{CH4[THC\text{-}FID]} + x_{C2H6} \times RF_{C2H6[THC\text{-}FID]} + x_{NMNEHC} \quad (2)$$

Expression (2) above is based on the assumption that the first analyzer 2 (THC-FID) is calibrated using propane $C_3H_8$ reference gas. Accordingly, $RF_{CH4[THC\text{-}FID]}$ and $RF_{C2H6[THC\text{-}FID]}$ are the methane and ethane response factors of the first analyzer 2 subjected to the propane calibration. In addition, a response factor is a sensitivity difference (ratio) of a target component from calibration gas. Further, the ethane response factor can be considered as 1.0, and therefore Expression (2) can be considered as the following expression.

$$x_{THC[THC\text{-}FID]} = x_{CH4} \times RF_{CH4[THC\text{-}FID]} + x_{C2H6} + x_{NMNEHC} \quad (3)$$

For the concentration obtained by the second analyzer 4 (NMNEC-FID), a concentration arithmetic expression is different depending on a calibration method.

(A) Case of Calibration with Propane Used and Bypassing NMNEC $$x_{THC[NMNEC\text{-}FID]} = x_{CH4} \times RF_{CH4[NMNEC\text{-}FID]} \times PF_{CH4[NMNEC\text{-}FID]} + x_{C2H6} \times RF_{C2H6[NMNEC\text{-}FID]} \times PF_{C2H6[NMNEC\text{-}FID]} + x_{NMNEHC} \times PF_{C3H8[NMNEC\text{-}FID]} \quad (4)$$

(B) Case of Calibration with Methane Used and Passed Through NMNEC $$x_{THC[NMNEC\text{-}FID]} = x_{CH4} \times x_{C2H6} \times RF_{C2H6[NMNEC\text{-}FID]} \times PF_{C2H6[NMNEC\text{-}FID]} + x_{NMNEHC} \times RF_{C3H8[NMNEC\text{-}FID]} \times PF_{C3H8[NMNEC\text{-}FID]} \quad (5)$$

(C) Case of Calibration with Methane Used and Bypassing NMNEC $$x_{THC[NMNEC\text{-}FID]} = x_{CH4} \times PF_{CH4[NMNEC\text{-}FID]} + x_{C2H6} \times RF_{C2H6[NMNEC\text{-}FID]} \times PF_{C2H6[NMNEC\text{-}FID]} + x_{NMNEHC} \times RF_{C3H8[NMNEC\text{-}FID]} \times PF_{C3H8[NMNEC\text{-}FID]} \quad (6)$$

(D) Case of Calibration with Ethane Used and Passing Through NMNEC $$x_{THC[NMNEC\text{-}FID]} = x_{CH4} \times RF_{CH4[NMNEC\text{-}FID]} \times PF_{CH4[NMNEC\text{-}FID]} + x_{C2H6} + x_{NMNEHC} \times RF_{C3H8[NMNEC\text{-}FID]} \times PF_{C3H8[NMNEC\text{-}FID]} \quad (7)$$

(E) Case of Calibration with Ethane Used and Bypassing NMNEC $$x_{THC[NMNEC\text{-}FID]} = x_{CH4} \times RF_{CH4[NMNEC\text{-}FID]} \times PF_{CH4[NMNEC\text{-}FID]} + x_{C2H6} \times PF_{C2H6[NMNEC\text{-}FID]} + x_{NMNEHC} \times RF_{C3H8[NMNEC\text{-}FID]} \times PF_{C3H8[NMNEC\text{-}FID]} \quad (8)$$

$x_{THC[NMNEC\text{-}FID]}$: Measured value of NMNEC-FID
$RF_{CH4[NMNEC\text{-}FID]}$: Methane response factor in NMNEC-FID $PF_{CH4[NMNEC-FID]}$: Methane penetrability in NMNEC-FID $RF_{C2H6[NMNEC-FID]}$: Ethane response factor in NMNEC-FID $PF_{C2H6[NMNEC-FID]}$: Ethane penetrability in NMNEC-FID $RF_{C3H8[NMNEC-FID]}$: Propane response factor in NMNEC-FID $PF_{C3H8[NMNEC-FID]}$: Propane penetrability in NMNEC-FID In Expressions (2) to (8) above, since the methane concentration and the ethane concentration cannot be measured, they have to be eliminated in order to simplify the concentration arithmetic expressions. Therefore, when focusing on Expressions (3) and (7), if $PF_{CH4[NMNEC-FID]}$ and $RF_{C3H8[THC-FID]}$ can be removed, these two expressions can be combined. In addition, in the case of using Expression (4), (5), (6), or (8), the methane concentration and the ethane concentration cannot be eliminated, and therefore the NMNEHC concentration cannot be calculated.

Further, since the NMNEC 3 is heated to 200 to 250° C., $PF_{CH4[THC-FID]}$ can be assumed to be approximately 1.0, and therefore removed from Expression (7).

Also, the propane response factor of the second analyzer 4 subjected to the ethane calibration can be considered as 1.0, and therefore removed from Expression (7).

As a result, the following expression can be obtained.

$$x_{THC[NMNEC-FID]} = x_{CH4} \times RF_{CH4[NMNEC-FID]} + x_{C2H6} + x_{NMNEHC} \times PF_{C3H8[NMNEC-FID]} \quad (9)$$

In addition, since the first analyzer 2 and the second analyzer 4 are the same in configuration, $RF_{CH4[THC-FID]}$ and $RF_{CH4[THC-FID]}$ can be considered as the same.

Accordingly, from Expressions (3) and (9), the following expression can be obtained.

$$x_{THC[THC-FID]} = x_{THC[NMNEC-FID]} - x_{NMNEHC} \times PF_{C3H8[NMNEC-FID]} + x_{NMNEHC} \quad (10)$$

By rewriting Expression (10) above in terms of $x_{NMNEHC}$, Expression (1) above can be derived. As described above, to derive Expression (1), the penetrability PF and response factor RF of each hydrocarbon component are taken into account.

From Expression (1) above, it turns out that by examining only $PF_{C3H8[THC-FID]}$, the NMNEHC concentration can be obtained from the concentration $x_{THC[THC-FID]}$ obtained by the first analyzer 2 (THC-FID) and the concentration $x_{THC[NMNEC-FID]}$ obtained by the second analyzer 4 (NMNEC-FID).

<Effects of the Present Embodiment>

Since the gas analysis apparatus 100 of the present embodiment can continuously measure the total methane ethane concentration of the methane and the ethane in the sample gas by the second analyzer 4 using the NMNEC 3 that removes the hydrocarbon components other than the methane and the ethane, the concentration of the hydrocarbon components other than the methane and the ethane in the sample gas can be calculated in combination with the THC concentration continuously measured by the first analyzer 2. As a result, the concentration of the hydrocarbon components other than the methane and the ethane (NMNEHC) in the sample gas can be continuously measured.

<Variations>

Note that the present invention is not limited to the above-described embodiment.

Figure 3:
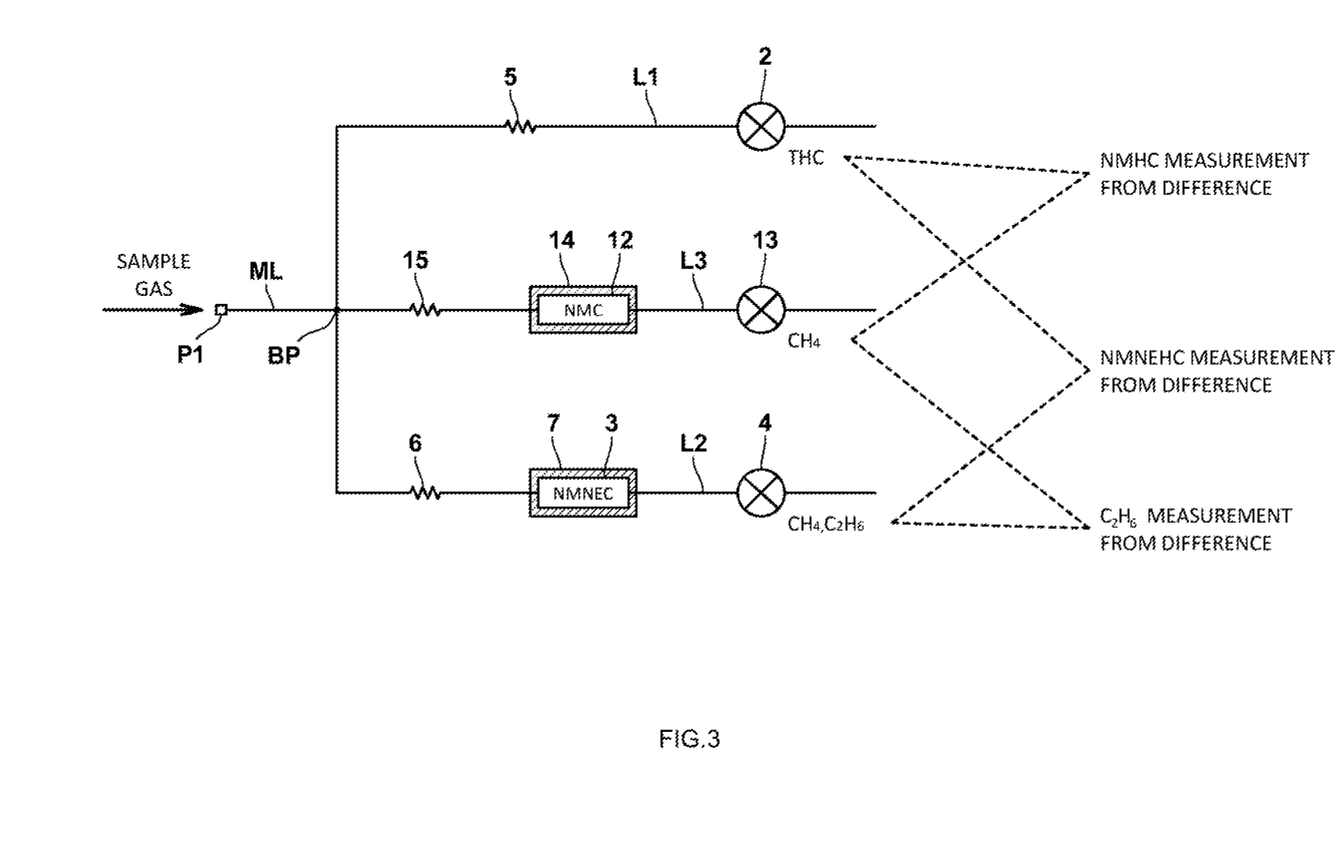
FIG. 3 is a diagram schematically illustrating the configuration of a gas analysis apparatus in a variation.

As illustrated in FIG. 3, the gas analysis apparatus 100 may further include: a third flow path L3 through which the sample gas flows and that is provided with a non-methane cutter (NMC) 12 for removing hydrocarbon components other than the methane in the sample gas; and a third analyzer 13 that is provided in the third flow path L3 to measure the methane concentration in the sample gas. In this case, the third flow path L3 is provided with a heating part 14 that increases the temperature of the NMC 12 to 300° C. or more.

In addition, the calculation part 11 can calculate the concentration of the hydrocarbon components other than the methane in the sample gas using the total hydrocarbon concentration by the first analyzer 2 and the methane concentration by the third analyzer 13. Further, the calculation part 11 can also calculate the ethane concentration in the sample gas using the total methane ethane concentration by the second analyzer 4 and the methane concentration by the third analyzer 13.

Still further, the third flow path L3 is provided with a third flow rate regulating mechanism 15 in order to match response timing among the first analyzer 2, the second analyzer 4, and the third analyzer 13. The third flow rate regulating mechanism 15 is formed of, for example, a capillary provided on the upstream side of the third analyzer 13 in the third flow path L3.

Figure 4:
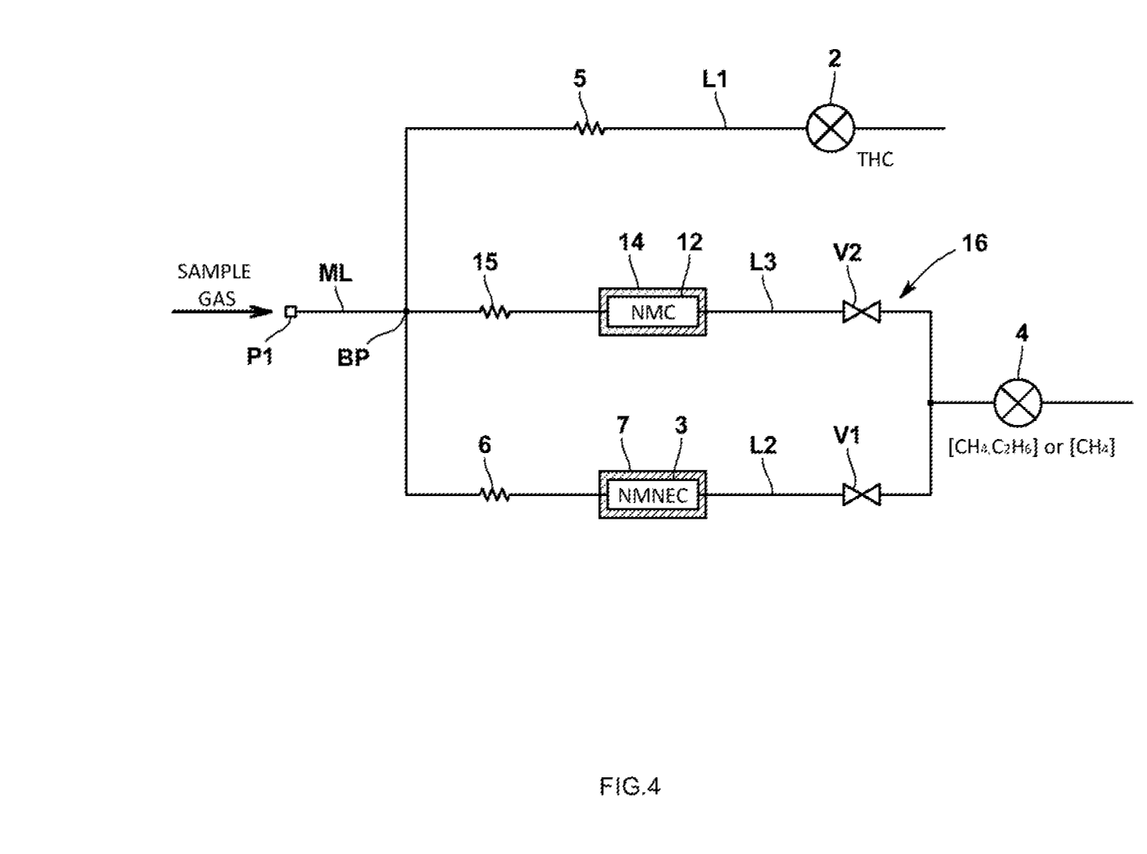
FIG. 4 is a diagram schematically illustrating the configuration of a gas analysis apparatus in a variation.

In addition, as illustrated in FIG. 4, the gas analysis apparatus 100 may be adapted to merge the downstream side of the NMC 12 in the third flow path L3 and the downstream side of the NMNEC 3 in the second flow path L2 and introduce the sample gas to the analyzer 4 in common. In this case, a flow path switching mechanism 16 that consists of, for example, on-off valves V1 and V2, and between the second flow path L2 and the third flow path L3, switches a flow path through which the sample gas flows is provided. Switching to the second flow path L2 allows the analyzer 4 to measure the total methane ethane concentration, and switching to the third flow path L3 allows the analyzer 4 to measure the methane concentration. This configuration makes it possible to reduce the number of analyzers, thus enabling cost reduction and the like of the gas analysis apparatus.

Without limitation to the configuration of the gas analysis apparatus of the above-described embodiment, the gas analysis apparatus of the present invention only has to include: a first flow path through which sample gas flows; a first analyzer that is provided in the first flow path to measure total hydrocarbon concentration in the sample gas; a second flow path through which the sample gas flows; a non-methane non-ethane cutter that is provided in the second flow path to remove hydrocarbon components other than methane and ethane in the sample gas; a second analyzer that is provided downstream of the non-methane non-ethane cutter in the second flow path to measure the total methane ethane concentration of the methane and the ethane in the sample gas; and a calculation part that calculates the concentration the hydrocarbon components other than the methane and the ethane in the sample gas with use of the total hydrocarbon concentration by the first analyzer and the total methane ethane concentration by the second analyzer.

Figure 5:
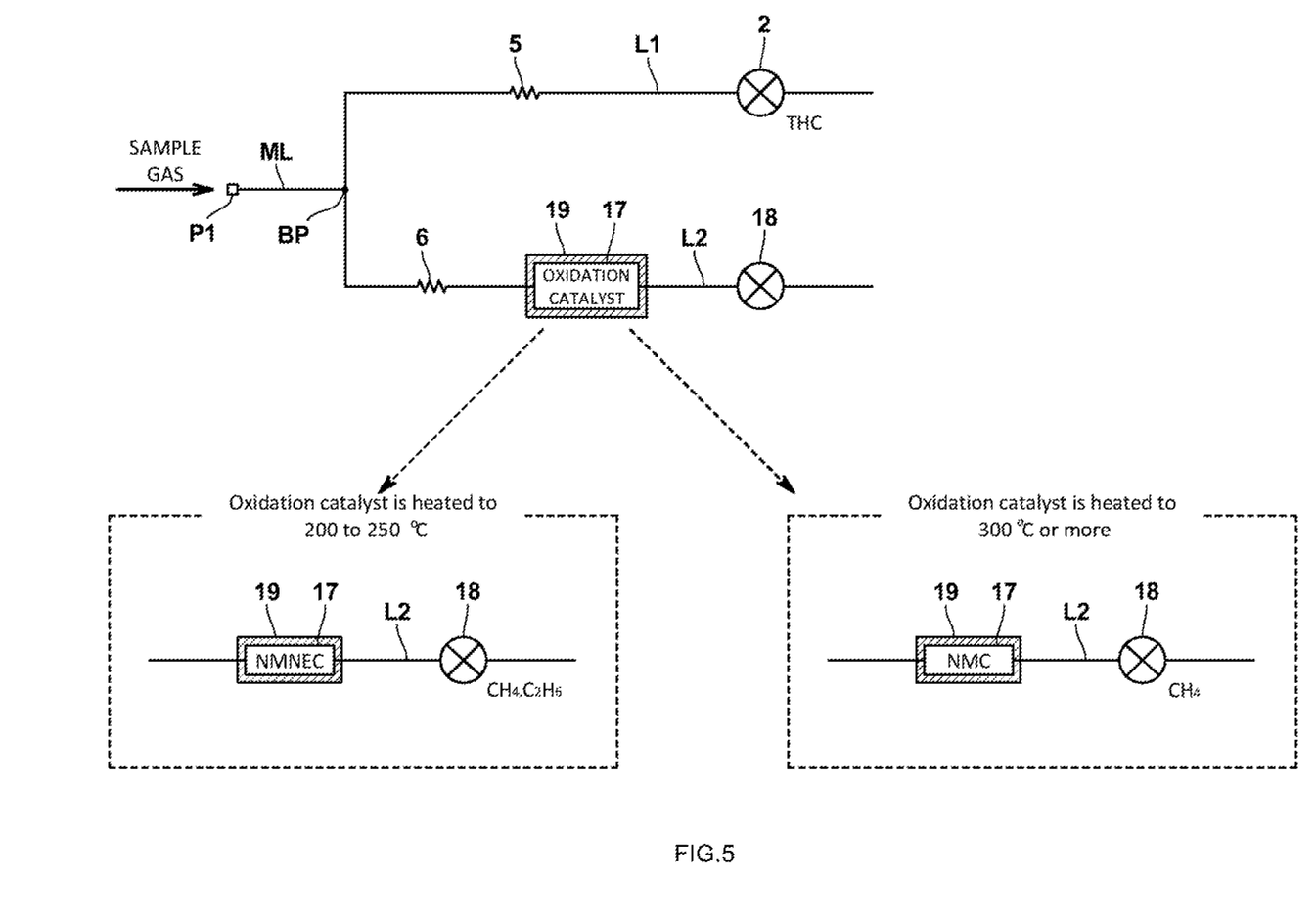
FIG. 5 is a diagram schematically illustrating the configuration of a gas analysis apparatus in a variation.

In addition, as illustrated in FIG. 5, the gas analysis apparatus 100 may include: a first flow path L1 through which exhaust gas as sample gas flows; a first analyzer 2 that is provided in the first flow path L1 to measure total hydrocarbon concentration (THC concentration) in the exhaust gas; a second flow path L2 that is provided separately from the first flow path L and through which the exhaust gas flows; a hydrocarbon selective catalyst 17 that is provided in the second flow path L2 to remove a predetermined hydrocarbon component in the exhaust gas; an analyzer 18 that is provided downstream of the hydrocarbon selective catalyst 17 in the second flow path L2 to measure the concentration of hydrocarbon components in the exhaust gas; and a temperature switching mechanism 19 that switches the temperature of the hydrocarbon selective catalyst 17. The analyzer 18 is an FID that detects the hydrocarbons in the exhaust gas by a hydrogen flame ionization (FID) method. The hydrocarbon selective catalyst 17 is a catalyst capable of, depending on a temperature, selecting a hydrocarbon component to be removed, and serves as, for example, a non-methane cutter or a non-methane non-ethane cutter depending on a temperature. In addition, the hydrocarbon selective catalyst 17 may be one that not only selectively removes methane, or methane and ethane, but can selectively remove another hydrocarbon. The temperature switching mechanism 19 is configured to include a heating part whose set temperature is changeable as in the above-described embodiment.

Further, the temperature switching mechanism 19 heats the hydrocarbon selective catalyst 17 to 200 to 250° C. to make the hydrocarbon selective catalyst 17 serve as a non-methane non-ethane cutter that removes hydrocarbon components other than methane and ethane in the exhaust gas. In doing so, the analyzer 18 measures the total methane ethane concentration of the methane and the ethane in the exhaust gas. In this case, a calculation part of the gas analysis apparatus 100 calculates the concentration of the hydrocarbon components other than the methane and the ethane in the exhaust gas from the THC concentration by the first analyzer 2 and the total methane ethane concentration by the analyzer 18.

Also, the temperature switching mechanism 19 heats the hydrocarbon selective catalyst 17 to 300° C. or more to make the hydrocarbon selective catalyst 17 serve as a non-methane cutter that removes hydrocarbon components other than the methane in the exhaust gas. In doing so, the analyzer 18 measures the concentration of the methane in the exhaust gas. In this case, the calculation part of the gas analysis apparatus 100 calculates the concentration of the hydrocarbon components other than the methane in the exhaust gas from the THC concentration by the first analyzer 2 and the methane concentration by the analyzer 18.

In addition, the temperature switching by the temperature switching mechanism 19 may be configured to be manually settable by a user or be automatically settable by, for example, a predetermined measurement sequence or the like. Further, in the above description, the analyzers 2, 4, and 18 are the FIDs; however, any analyzer can be used as long as the analyzer can measure hydrocarbon components.

Besides, various modifications and combinations of the embodiment and the variations may be made without departing from the scope of the present invention.

REFERENCE SIGNS LIST

100: Gas analysis apparatus
L1: First flow path
2: First analyzer
L2: Second flow path
3: Non-methane non-ethane cutter (NMNEC)
4: Second analyzer
5: First flow rate regulating mechanism
6: Second flow rate regulating mechanism
7: Heating part
11: Calculation part
L3: Third flow path
12: Non-methane cutter (NMC)
13: Third analyzer
14: Heating part
15: Third flow rate regulating mechanism
17: Hydrocarbon selective catalyst
18: Analyzer
19: Temperature switching mechanism

The invention claimed is:

1. A gas analysis apparatus comprising:
  a first flow path through which sample gas flows;
  a first analyzer that is provided in the first flow path to measure total hydrocarbon concentration in the sample gas;
  a second flow path through which the sample gas flows;
  a non-methane non-ethane cutter that is provided in the second flow path to remove hydrocarbon components other than methane and ethane in the sample gas;
  a second analyzer that is provided downstream of the non-methane non-ethane cutter in the second flow path to measure total methane ethane concentration of the methane and the ethane in the sample gas; and
  a calculation part that calculates concentration of the hydrocarbon components other than the methane and the ethane in the sample gas with use of the total hydrocarbon concentration by the first analyzer and the total methane ethane concentration by the second analyzer.

2. The gas analysis apparatus according to claim 1, wherein
  the second analyzer is calibrated with ethane used and passed through the non-methane non-ethane cutter.

3. The gas analysis apparatus according to claim 1, wherein
  the calculation part calculates the concentration of the hydrocarbon components other than the methane and the ethane in the sample gas with use of the total hydrocarbon concentration by the first analyzer, the total methane ethane concentration by the second analyzer, and specific organic matter penetrability that is a ratio at which specific organic matter having a carbon number of 3 or more passes through the non-methane non-ethane cutter.

4. The gas analysis apparatus according to claim 1, wherein
  the calculation part calculates the concentration of the hydrocarbon components other than the methane and the ethane in the sample gas in accordance with an expression below:

[Expression 4]

$$x_{NMNEHC} = \frac{x_{TCH[THC-FID]} - x_{THC[NMNEC-FID]}}{1 - PF_{C_3H_8[HMNEC-FID]}}$$

$x_{NMNEHC}$: the concentration of the hydrocarbon components other than the methane and the ethane in the sample gas
$x_{THC[THC-FID]}$: the total hydrocarbon concentration by the first analyzer
$x_{THC[NMNEC-FID]}$: the total methane ethane concentration by the second analyzer
$PF_{C_3H_8[THC-FID]}$: the specific organic matter penetrability that is a ratio at which the specific organic matter having a carbon number of 3 or more passes through the non-methane non-ethane cutter.

5. The gas analysis apparatus according to claim 1, wherein
the second flow path is provided with a heating part that increases temperature of the non-methane non-ethane cutter to 200 to 250° C.

6. The gas analysis apparatus according to claim 1, further comprising:
a first flow rate regulating mechanism provided in the first flow path; and
a second flow rate regulating mechanism provided in the second flow path, wherein
the first flow rate regulating mechanism and the second flow rate regulating mechanism match response timing between the first analyzer and the second analyzer.

7. The gas analysis apparatus according to claim 1, further comprising:
a third flow path through which the sample gas flows;
a non-methane cutter that is provided in the third flow path to remove hydrocarbon components other than the methane in the sample gas; and
a third analyzer that is provided downstream of the non-methane cutter in the third flow path to measure methane concentration in the sample gas.

8. The gas analysis apparatus according to claim 7, wherein
the calculation part calculates concentration of the hydrocarbon components other than the methane in the sample gas with use of the total hydrocarbon concentration by the first analyzer and the methane concentration by the third analyzer.

9. The gas analysis apparatus according to claim 7, wherein
the calculation part calculates ethane concentration in the sample gas with use of the total methane ethane concentration by the second analyzer and the methane concentration by the third analyzer.

10. The gas analysis apparatus according to claim 7, wherein
the third flow path is provided with a heating part that increases temperature of the non-methane cutter to 300° C. or more.

11. The gas analysis apparatus according to claim 10, further comprising
a third flow rate regulating mechanism provided in the third flow path, wherein
the first flow rate regulating mechanism, the second flow rate regulating mechanism, and the third flow rate regulating mechanism match response timing among the first analyzer, the second analyzer, and the third analyzer.

12. A gas analysis apparatus calibration method for the gas analysis apparatus according to claim 1,
the gas analysis apparatus calibration method calibrating the second analyzer with ethane used and passed through the non-methane non-ethane cutter.

13. The gas analysis apparatus calibration method according to claim 12,
calibrating the first analyzer with use of propane.

14. A gas analysis method using the gas analysis apparatus according to claim 1,
the gas analysis method
using Expression (A) below in a case where the first analyzer is calibrated with use of propane:

$$x_{THC[THC-FID]} = x_{CH4} \times RF_{CH4[THC-FID]} + x_{C2H6} \times RF_{C2H6[THC-FID]} + x_{NMNEHC} \quad \text{Expression (A):}$$

$x_{THC[THC-FID]}$: the total hydrocarbon concentration by the first analyzer
$x_{CH4}$: methane concentration in the sample gas
$RF_{CH4[THC-FID]}$: a methane response factor in the first analyzer
$x_{C2H6}$: ethane concentration in the sample gas
$RF_{C2H6[THC-FID]}$: an ethane response factor in the first analyzer
$x_{NMNEHC}$: concentration of the hydrocarbon components other than the methane and the ethane in the sample gas, and
Expression (B) below in a case where the second analyzer is calibrated with ethane used and passed through the non-methane non-ethane cutter $$x_{THC[NMNEC-FID]} = x_{CH4} \times RF_{CH4[NMNEC-FID]} \times PF_{CH4[NMNEC-FID]} + x_{C2H6} + x_{NMNEHC} \times RF_{C3H8[NMNEC-FID]} \times PF_{C3H8[NMNEC-FID]} \quad \text{Expression (B):}$$

$x_{THC[NMNEC-FID]}$: the total methane ethane concentration by the second analyzer
$RF_{CH4[NMNEC-FID]}$: a methane response factor in the second analyzer
$RF_{C3H8[NMNEC-FID]}$: methane penetrability in the second analyzer
$RF_{C3H8[NMNEC-FID]}$ a propane response factor in the second analyzer $PF_{C3H8[NMNEC-FID]}$: propane penetrability in the second analyzer to derive Expression (1) below:

[Expression 5]

$$x_{NMNEHC} = \frac{x_{THC[THC-FID]} - x_{THC[NMNEC-FID]}}{1 - PF_{C_3H_8[NMNEC-FID]}} \quad (1)$$

$x_{NMNEHC}$: the concentration of the hydrocarbon components other than the methane and the ethane in the sample gas
$x_{THC[THC-FID]}$: the total hydrocarbon concentration by the first analyzer
$x_{THC[NMNEC-FID]}$: the total methane ethane concentration by the second analyzer
$PF_{C3H8[NMNEC-FID]}$: specific organic matter penetrability that is a ratio at which specific organic matter having a carbon number of 3 or more (in this case, propane $C_3H_8$) passes through the non-methane non-ethane cutter, and
calculating the concentration of the hydrocarbon components other than the methane and the ethane in the sample gas with use of Expression (1) above.

15. The gas analysis method according to claim 14,
in the Expression (A), considering the ethane response factor $RF_{C2H6[THC-FID]}$ as 1.0 to derive Expression (A') below:

$$x_{THC[THC-FID]} = x_{CH4} \times RF_{CH4[THC-FID]} + x_{C2H6} + x_{NMNEHC} \quad \text{Expression (A'):}$$

in the Expression (B), considering $PF_{CH4[NMNEC-FID]}$ as 1.0, and also considering the propane response factor in the second analyzer subjected to ethane calibration as 1.0 to derive Expression (B') below:

$$x_{THC[NMNEC-FID]} = x_{CH4} \times RF_{CH4[NMNEC-FID]} + x_{C2H6} + x_{NMNEHC} \times PF_{C3H8[NMNEC-FID]} \quad \text{Expression (B'):}$$

deriving Expression (C) below because when the first analyzer and the second analyzer are the same in configuration, $RF_{CH4[THC-FID]}$ and $RF_{CH4[NMNEC-FID]}$ are the same:

$$x_{THC[THC\text{-}FID]} = x_{THC[NMNEC\text{-}FID]} - x_{NMNEHC} \times PF_{C3H8[NMNEC\text{-}FID]} + x_{NMNEHC} \quad \text{Expression (C):}$$

and deriving Expression (1) above from Expression (C).

16. A gas analysis apparatus comprising
a flow path through which sample gas flows;
a hydrocarbon selective catalyst that is provided in the flow path to remove a predetermined hydrocarbon component in the sample gas;
an analyzer that is provided downstream of the hydrocarbon selective catalyst in the flow path to measure concentration of hydrocarbon components in the sample gas; and
a temperature switching mechanism that switches temperature of the hydrocarbon selective catalyst, wherein
the temperature switching mechanism heats the hydrocarbon selective catalyst to 200 to 250° C. to make the hydrocarbon selective catalyst serve as a non-methane non-ethane cutter that removes hydrocarbon components other than methane and ethane in the sample gas, and heats the hydrocarbon selective catalyst to 300° C. or more to make the hydrocarbon selective catalyst serve as a non-methane cutter that removes hydrocarbon components other than the methane in the sample gas.

17. A gas analysis method:
providing a first analyzer in a first flow path through which sample gas flows, the first analyzer measuring total hydrocarbon concentration in the sample gas;
providing a non-methane non-ethane cutter in a second flow path through which the sample gas flows, the non-methane non-ethane cutter removing hydrocarbon components other than methane and ethane in the sample gas;
providing a second analyzer downstream of the non-methane non-ethane cutter in the second flow path, the second analyzer measuring total methane ethane concentration of the methane and the ethane in the sample gas; and
calculating concentration of the hydrocarbon components other than the methane and the ethane in the sample gas with use of the total hydrocarbon concentration by the first analyzer and the total methane ethane concentration by the second analyzer.

* * * * *